(12) United States Patent
Schmid

(10) Patent No.: US 7,272,426 B2
(45) Date of Patent: Sep. 18, 2007

(54) FINGER MEDICAL SENSOR

(75) Inventor: Alfons Schmid, Böblingen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 190 days.

(21) Appl. No.: 10/544,353

(22) PCT Filed: Jan. 30, 2004

(86) PCT No.: PCT/IB2004/000217

§ 371 (c)(1),
(2), (4) Date: Aug. 3, 2005

(87) PCT Pub. No.: WO2004/069046

PCT Pub. Date: Aug. 19, 2004

(65) Prior Publication Data

US 2006/0155198 A1    Jul. 13, 2006

(30) Foreign Application Priority Data

Feb. 5, 2003    (EP) .................................. 03100237

(51) Int. Cl.
*A61B 5/00*    (2006.01)
(52) U.S. Cl. .................................................. 600/344
(58) Field of Classification Search ................ 600/310, 600/323, 340, 344
See application file for complete search history.

(56) References Cited

U.S. PATENT DOCUMENTS

| | | | |
|---|---|---|---|
| 3,810,460 A | 5/1974 | Van Nie | |
| 4,109,643 A | 8/1978 | Bond et al. | |
| 4,685,464 A | 8/1987 | Goldberger et al. | |
| 5,311,865 A | 5/1994 | Mayeux | |
| 5,511,546 A | 4/1996 | Hon | |
| 5,596,986 A | 1/1997 | Goldfarb | |
| 5,817,010 A | 10/1998 | Hibl | |

FOREIGN PATENT DOCUMENTS

| | | |
|---|---|---|
| DE | 37 03 458 C2 | 8/1988 |
| EP | 0 127 947 A2 | 12/1984 |
| WO | WO 92/21281 A1 | 12/1992 |

*Primary Examiner*—Eleni Mantis-Mercader
*Assistant Examiner*—Etsub D Berhanu

(57) ABSTRACT

The present invention relates to a medical sensor (1) for measuring pulse, blood, tissue and/or skin parameters using electromagnetic waves in the transmission method, comprising a carrier part (2) for pushing onto a patient's finger or toe. A first carrier leg (12) carries a transmitter unit (5) and a second carrier leg (13) carries a receiver unit (6). A carrier base (14) connects the two carrier legs (12, 13) to one another in the region of a tip of the finger or toe. A spring part (3) is arranged on the outside of the carrier part (2) such that a first spring leg (15) bears against the first carrier leg (12) and a second spring leg (16 bear against the second carrier leg (13). The carrier part (2) is made of a more flexible material than the spring part (3), in which the spring legs (15, 16) prestress the carrier legs (12, 13) toward one another.

20 Claims, 2 Drawing Sheets

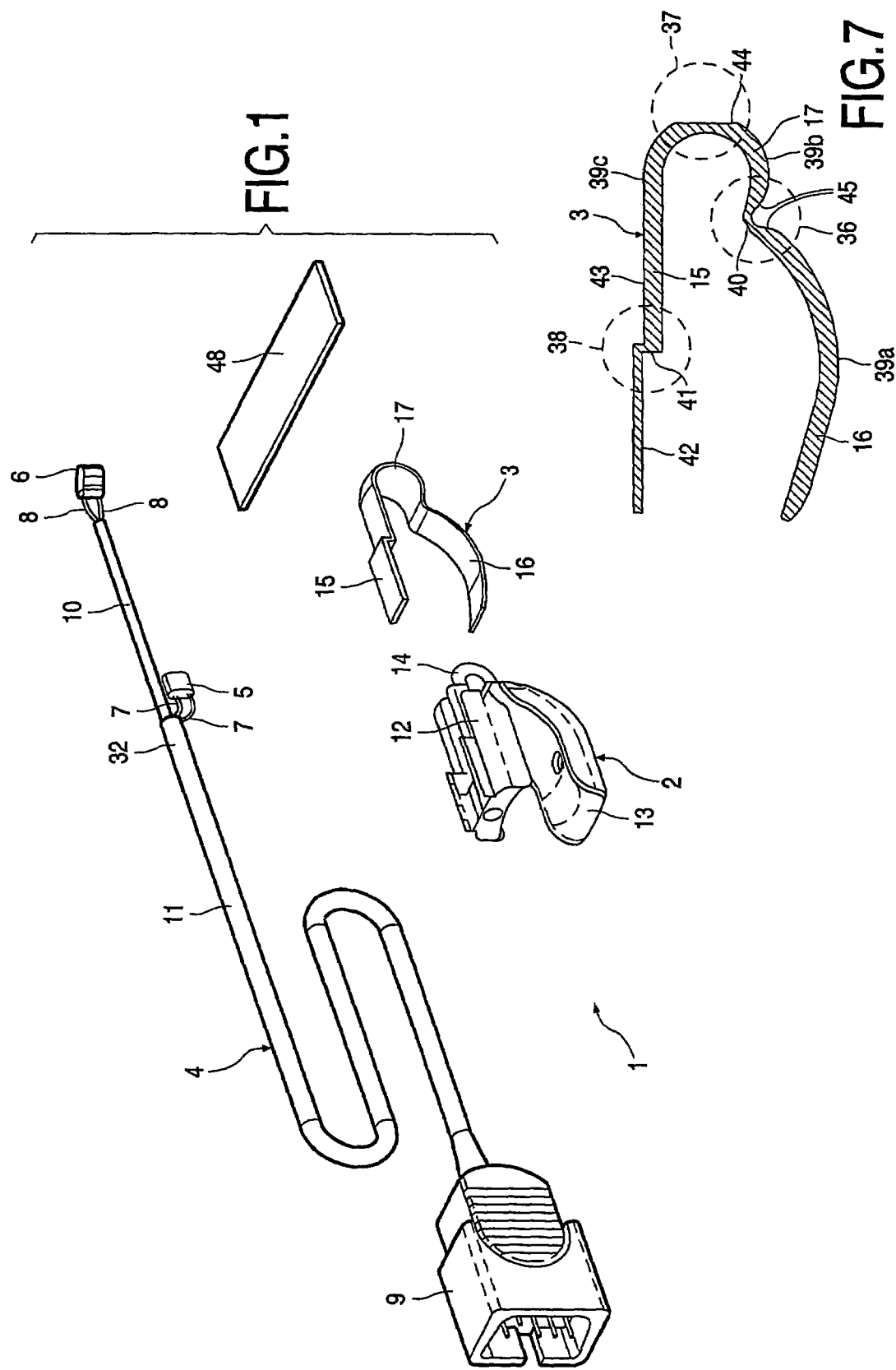

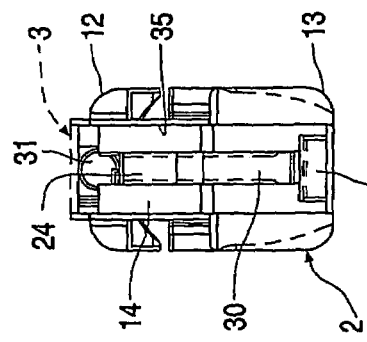
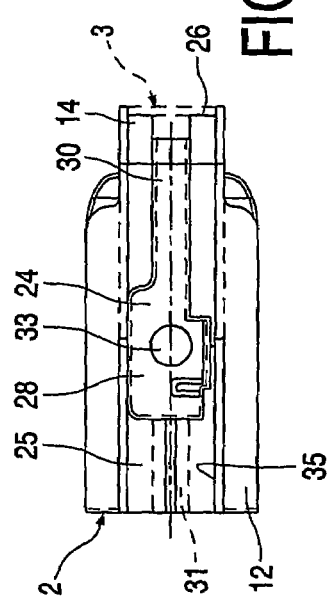
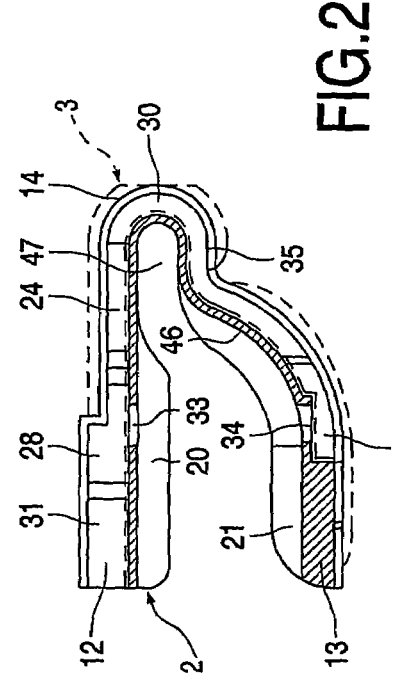
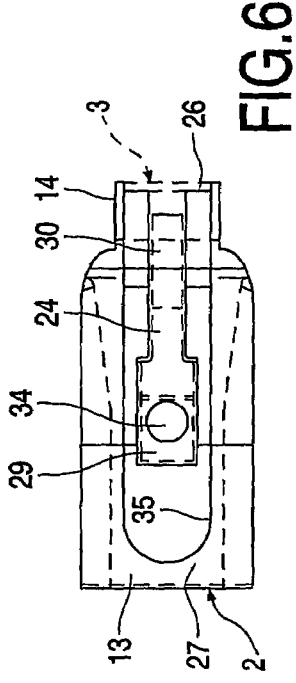
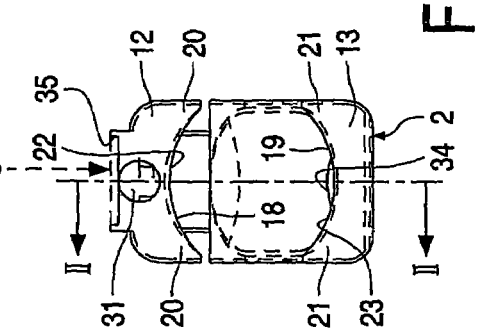

FINGER MEDICAL SENSOR

The present invention relates to a medical sensor for measuring pulse, blood, tissue and/or skin parameters using electromagnetic waves in the transmission method.

During an operation or during a stay in intensive care, it may be expedient to check and monitor inter alia the lung function, metabolism and heart rate of the patient. This may be carried out, for example, by measuring the oxygen saturation and the pulse rate. Sensors of the type mentioned above are used for this, and these can be used to carry out a measurement, derived from the pulse, of the arterial oxygen saturation by means of an optoelectronic transmission measurement. Such a sensor often includes at least one transmitter, for example a light-emitting diode, or LED for short, with infrared light and an LED with red light, and also at least one receiver, usually a photodiode, and a carrier assembly which positions the transmitter and the receiver in the desired manner on a finger or toe of the patient.

With these sensors, a distinction is made between single-use sensors, semi-reusable sensors and reusable sensors.

In patients of different size, the diameter of the fingers and toes is considerably different. Accordingly, the patients are divided up into groups in terms of their size, for example large adult, adult, small adult and child.

A sensor that is designed as an adhesive sensor is known from EP 0 127 947 B1, in which the carrier component consists essentially of an adhesive tape which is wound around the finger or toe and stuck thereto. Although such adhesive sensors are designed as disposable sensors, they are relatively expensive on account of their complex manufacture. In order to obtain correct measurement results, the adhesive sensors must be positioned carefully depending on the size of the respective finger and/or toe. In order to simplify or allow attachment of the adhesive sensors to patients of different size, the adhesive sensors are usually available in different sizes.

Sensors designed as clip sensors, which in each case have two legs mounted on one another in a manner such that they can pivot about a pivot spindle, are known from U.S. Pat. No. 3,810,460 and U.S. Pat. No. 4,685,464. One of the legs contains the transmitter while the other leg contains the receiver. In the known clip sensors, the transmission direction of the transmitter and the receiving direction of the receiver change as a function of the pivot angle between the clip legs. The known clip sensors may therefore supply reliable measurement results only within predefined, relatively narrow angle ranges. Accordingly, the clip sensors must be provided in various sizes for patients of different size. In addition, at large opening widths, the pressure on the finger or toe that is generated by the clamping legs becomes so great that it obstructs the blood supply and falsifies the measurement. The clip sensors are constructed in a relatively complex manner and may therefore only be provided as reusable sensors.

Other sensors which are designed as sleeve sensors are known from DE 37 03 458 C2 and U.S. Pat. No. 4,109,643. In sleeve sensors, the carrier component is designed as a sleeve which can be pushed onto the finger or toe and then surrounds the latter on all sides. However, the opening width of the sleeves can be changed only to a relatively limited extent. In the case of relatively large fingers or toes, the pressure becomes so great that the blood flow in the finger or toe is obstructed. In the case of relatively small fingers or toes, the contact with the surface may be lost, so that in this case too no measurements are possible. Furthermore, these sleeve sensors are constructed in a relatively complex manner, so that they are expensive to manufacture and are used only as reusable sensors.

A common feature of the known sensors is that they are suitable only as reusable sensors on account of their complex design and/or to achieve a sufficiently high functional reliability must be provided in various sizes in order to be able to carry out the desired measurements on patients of different size.

The object of the present invention is to specify an improved embodiment for a medical sensor of the type mentioned in the introduction, which makes it possible in particular to carry out the necessary measurements on a number of, preferably all, conventional patients with one sensor size. Furthermore, it should be possible to manufacture the sensor in such an economical manner that is can be provided as a disposable sensor.

This object is achieved according to the invention by the subject matter of the independent claim. Advantageous embodiments form the subject matter of the dependent claims.

The invention is based on the general concept of equipping the sensor with a clip-like flexible carrier part and a likewise clip-like, but more rigid, spring part, where the relatively flexible carrier part carries the transmitter and the receiver on opposite carrier legs while the relatively hard spring part prestresses the carrier legs toward one another by virtue of opposite spring legs. By means of the proposed design, the functions "holding and positioning of the transmitter and receiver" and "retaining of the sensor on the finger or toe" are distinct from one another and assigned to different components. As a result, it is possible to optimize the various components in relation to their function. According to the invention, the carrier part is designed to be more flexible than the spring part, as a result of which the carrier part can adapt better to the finger or toe that is inserted in each case. By contrast, by means of a spring force the spring part generates the necessary retaining forces to keep the sensor on the respectively inserted finger or toe.

The sensor according to the invention in principle operates like a clip sensor but does not require a positioning spindle and can accordingly be manufactured in an economical manner. By configuring the carrier part and the spring part with in each case two legs which are connected to one another by a base, the sensor can be dimensioned relatively simply in a manner such that it can be used for a relatively large finger or toe diameter range.

A particularly economical manufacture results when the carrier part is made in one piece and/or when the spring part is made in one piece. Carrier part and/or spring part may then be manufactured in large numbers economically, as a result of which the manufacturing costs for the sensor are considerably reduced.

One embodiment in which the spring part has at least one spring zone which connects together two support sections that adjoin it, said support sections being more rigid than the spring zone, is particularly advantageous. By means of this design, the spring characteristic of the spring part can be deliberately configured such that there are restoring forces that are adapted to the opening widths.

When the spring part has two or more spring zones, it may be advantageous for these to be configured with different rigidities. This measure also simplifies the adaptation of the spring characteristic of the sensor to the requirements of different finger or toe diameters.

An embodiment in which the support sections which adjoin the more flexible spring zone form a stop which restricts the bending deformation in this spring zone to a predefined extent during widening of the carrier legs is of particular interest. On account of this design, by means of the stop in the spring characteristic of the sensor, a step is realized in which the rigidity of the spring part changes in the manner of a jump. On account of this design, the adaptation of the restoring forces to the requirements of differently sized fingers or toes is improved.

A further important embodiment is characterized in that on the outside of the carrier part there is a groove which extends from the outer side of the first carrier leg via an outer side of the carrier base to the outer side of the second carrier leg, in which the at least one transmitting element and the at least one receiving element are arranged and in which connection cables for the transmitting element and the receiving element are laid, wherein the spring part closes this groove from outside. In this design, the optoelectronic components and their cables can be accommodated in the carrier part in a relatively simple manner. The secure holding thereof on the carrier part is then ensured by the fitted spring part, as a result of which the spring part is given an additional function. The assembly of the sensor is simplified thereby.

Further important features and advantages of the invention emerge from the dependent claims, the drawings and the associated description of the figures with reference to the drawings;

It will be understood that the features which have been mentioned above and are yet to be mentioned below can be used not only in the combination respectively specified but also in other combinations or alone without departing from the scope of the present invention.

The invention will be further described with reference to examples of embodiments shown in the drawings to which, however, the invention is not restricted. The same references relate to identical or functionally identical or similar components.

FIG. 1 shows a perspective view of the individual parts of a sensor according to the invention.

FIG. 2 shows a longitudinal section through a carrier part of the sensor on section line II in FIG. 3.

FIG. 3 shows a view of the carrier part from the front.

FIG. 4 shows a view of the carrier part from behind.

FIG. 5 shows a view of the carrier part from above.

FIG. 6 shows a view of the carrier part from below.

FIG. 7 shows a longitudinal section as in FIG. 2, but through a spring part of the sensor.

As shown in FIG. 1, a medical sensor 1 according to the invention comprises a carrier part 2, a spring part 3 and a signal transmission unit 4. In addition, a fixing strip or fixing tape 48 may be provided. The sensor 1 is used to measure pulse, blood, tissue and/or skin parameters on a finger or toe of a patient. The sensor 1 is additionally used for measuring the oxygen saturation, with it being possible for the pulse rate to be determined at the same time. The sensor 1 operates using electromagnetic waves, preferably with visible and/or invisible light. The sensor 1 operates according to the transmission principle, in which the electromagnetic waves of at least one transmitting element are irradiated into the finger or toe and the waves emerging from the finger or toe on the opposite side are measured and evaluated by means of at least one receiving element.

For this purpose, the signal transmission unit 4 comprises a transmitter unit 5 comprising at least one transmitting element that is not discussed in any more detail here. Such a transmitting element may be formed for example of an LED. The signal transmission unit 4 further comprises a receiver unit 6 which comprises at least one receiving element that is not discussed in any more detail here. Such a receiving element may be for example a photodiode. The transmitter unit 5 or its transmitting elements and the receiver unit 6 or its receiving elements are connected to a plug 9 of the signal transmission unit 4 via first cables 7 and second cables 8, respectively. The individual second cables 8 of the receiver unit 6 are in this case combined to form a collective cable 10. The collective cable 10 and the individual first cables 7 of the transmitter unit 5 are combined to form a common cable 11 which leads to the plug 9.

The carrier part 2 is designed in the manner of a clip and accordingly has two carrier legs which lie opposite one another, namely a first carrier leg 12 and a second carrier leg 13. In FIG. 1, the two carrier legs 12, 13 are connected to one another on a side remote from the observer by a carrier base 14. In the preferred embodiment shown here, the carrier part 2 is produced as one piece. The carrier part 2 is made of a relatively soft, elastically deformable material. The shaping of the carrier part 2 or of its carrier legs 12, 13 is selected such that the carrier part 2 can be pushed onto the patient's finger or toe from the front. The carrier base 14 is then located in the region of a tip of the finger or toe during the measurement operation.

The spring part 3 has essentially the same contour as the carrier part 2. Specifically, the spring part 3 is likewise designed in the manner of a clip and accordingly has two spring legs, namely a first spring leg 15 and a second spring leg 16. The spring legs 15, 16 are also connected to one another on one side by a spring base 17. The spring part 3 is preferably also produced in one piece, but is made of a relatively hard, elastically deformable material. The terms "relatively soft" and "relatively hard" relate to the relations between the carrier part 2 and the spring part 3.

As shown in FIGS. 2 to 6, the carrier legs 12, 13 are in each case curved concavely toward one another on inner sides 18, 19 that face one another. Accordingly, each carrier leg 12 has two laterally outwardly lying side cheeks 20 and 21 which in each case project from a central zone 22 or 23 toward the respectively opposite carrier leg 12, 13. As can be seen from FIG. 3, the side cheeks 20 of the first carrier leg 12 and the side cheeks 21 of the second carrier leg 13 are in alignment with one another, so that the carrier legs 12, 13 make contact with one another at their side cheeks 20, 21 in an initial state in which they are pressed together to a maximum extent.

The carrier part 2 on the outside contains a groove 24 which extends from an outer side 25 of the first carrier leg 12 via an outer side 26 of the carrier base 14 to an outer side 27 of the second carrier leg 13. In the first carrier leg 12, the groove 24 forms a first recess 28 for accommodating the transmitter unit 5. In the second carrier leg 13, the groove 24 forms a second recess 29 for accommodating the receiver unit 6. Between the two recesses 28, 29, the groove 24 forms a cable channel 30 in which the second cables 8 or the collective cable 10 can be laid. The first carrier leg 12 contains a further cable channel 31 which leads from a front side of the first carrier leg 12 that is remote from the carrier base 14 to the recess 28. In this further cable channel 31 there may be laid an end section 32 (cf. FIG. 1) of the common cable 11. The first recess 28 contains a transmission opening 33 through which the at least one transmitting element can irradiate the electromagnetic waves to the receiver unit 6. In a corresponding manner, the second recess 29 contains a receiving opening 34 through which the at least one receiving element can receive the waves emitted by the transmitter unit 5.

To assemble the sensor 1, the end section 32 of the common cable 11 is introduced into the further cable channel 21 and expediently fixed therein, for example by clamping or adhesive bonding. The transmitter unit 5 is inserted into the first recess 28 and expediently fixed therein, e.g. by adhesive bonding. Furthermore, the receiver unit 6 is inserted into the second recess 29 and expediently fixed therein, e.g. by adhesive bonding. The collective cable 11 is laid in the cable channel 30. The spring part 3 is then placed on the outside of the carrier part 2. The spring part 3 serves as a closure or cover for the groove 24. This means that the assembled spring part 3 covers or closes the recesses 28, 29 and the cable channels 30, 31. The spring part 3 is also expediently fixed in a suitable manner on the carrier part 2, for example by welding. On the outside, the carrier part 2 has a receiving contour 35 that is adapted to the contour of the spring part 3. The spring part 3 is thereby at least partly sunk into the outside of the carrier part 2 and laterally fixed by the receiving contour 35.

In FIGS. 2 to 6, the spring part 3 attached to the carrier part 2 is shown by broken lines.

As shown in FIG. 7, the clip-like spring part 3 is also expediently produced as one piece. In this case, the spring part 3 is made of a material that is elastically, in particularly spring-elastically, deformable but has a greater rigidity than the material of the carrier part 2. Compared to the carrier part 2, the spring part 3 is thus made of a hard material.

The spring part 3 has at least one spring zone, in this case two spring zones, namely a first spring zone 36 and a second spring zone 37. Each spring zone 36 and 37 connects together two support sections 39 of the spring part 3 which adjoin it. Specifically, the first spring zone 36 connects a first support section 39a to a second support section 39b, while the second spring zone 37 connects the second support section 39b to a third support section 39c. The configuration of the spring zones 36, 37 is selected such that the spring zones 36, 37 are in each case more flexible than the adjacent support sections 39. This means that the support sections 39 are more rigid than the spring zones 36, 37 arranged therebetween.

In the preferred embodiment shown here, the first spring zone 36 is made at a transition 40 between the second spring leg 16 and the spring base 17. The first spring zone 36 is in this case formed by a material contraction, as a result of which the first spring zone 36 has a comparatively low spring elasticity.

The second spring zone 37 is in this case made approximately in the middle of the spring base 17. The second spring zone 37 is realized by a flattening 44 which reduces the wall thickness of the spring base 17 in the region of the second spring zone 37. The second spring zone 37 is configured such that its rigidity is greater than that of the first spring zone 36.

The first spring leg 15 in this case comprises two sections, namely an end section 42 and a start section 43. While the start section 43 directly adjoins the spring base 17, the end section 42 is remote from the spring base 17. The two sections 42, 43 are differentiated from one another in that the end section 42 is more flexible than the start section 43. This is achieved in this instance by different material thicknesses. As can be seen from FIG. 7, the end section 42 adjoins the start section 43 in a region 38. This region 38 is positioned along the first spring leg 15 in a manner such that it is arranged approximately in the center with respect to the second spring leg 16. Usually, then, this region 38 is located in a position in which a fingernail or toenail end that is remote from the finger tip or toe tip of the finger or toe inserted in the sensor 1 is located. The transition between the two sections 42, 43 is in this case formed by a step 41 in the region 38. The spring elasticity of the end section 42 is expediently matched to the spring elasticities of the first spring zone 36 and of the second spring zone 37. The end section 42 is expediently more rigid than the second spring zone 37. The two spring zones 36, 37 and the relatively flexible end section 42 form three preferred bending zones within the spring part 3, which bending zones deform elastically to a greater extent than the adjoining support sections 39a, 39b, 39c during widening of the spring legs 15, 16.

The sensor 1 according to the invention operates as follows:

In an initial position, that is to say before the sensor 1 is pushed onto a finger or toe, the spring part 3 causes the sensor 1 or the carrier part 2 to assume an initial state. In the assembled sensor 1, the spring legs 15, 16 bear against the outer sides 25 and 27 of the carrier legs 12, 13 and stress them in the direction of one another. The spring part 3 is designed such that it causes the carrier legs 12, 13 to bear against one another at their side cheeks 20, 21 in the initial state. The sensor 1 may expediently be dimensioned such that it can be pushed onto the finger or toe of a child in such a manner that the two carrier legs 12, 13 lift off one another. It is thus ensured that a desired application force for the carrier legs 12, 13 against the finger or toe can be achieved even in the case of small fingers or toes. When the carrier legs 12, 13 are widened, the first spring zone 36 is initially deformed to the greatest extent. The resulting restoring forces are relatively small. Thus even in the case of children who normally have a lower blood pressure than adults the restoring force does not lead to any disruptive influencing of the blood flow and pulse. Nevertheless, the restoring forces generate a sufficient pressure to fix the sensor 1 sufficiently on the finger or toe.

When the sensor 1 is attached to a larger child or to a small adult, the second carrier leg 13 can pivot out to a wide enough extent, with the restoring forces accordingly increasing the spring characteristic of the spring part 3.

In the case of an average-sized adult, the bending deformation of the first bending zone 36 reaches a predetermined value during widening of the carrier legs 12, 13, said predetermined value being delimited or defined by a stop 45 in the specific embodiment of the spring part 3 shown here in FIG. 7. This stop 45 is formed by flanks of the support sections 39a, 39b which adjoin the first spring zone 36, these flanks coming to bear against one another when the predetermined bending deformation is reached, thus preventing further bending deformation in the first spring zone 36. By means of this special design, the spring characteristic of the spring part 3 at this point exhibits a jump. This is because, while below this limit bending deformation there is almost a serial connection of the rigidities of the three bending zones 36, 37, 42, above said bending deformation there is only a serial connection of the rigidities of the second spring zone 37 and of the end section 42. This means that during bending of the carrier legs 12, 13, the restoring forces increase to a lesser extent up until the predetermined bending deformation is reached than in the case of a more extensive widening of the carrier legs 12, 13. Such a more extensive widening is achieved when the sensor 1 is used on a normal adult or on a large adult. In those cases, greater restoring forces are also required in order to be able to obtain correct measurement results.

In the case of large adults, the bending deformation in the second spring zone 37 may also reach a limit value, in which the spring elasticity of the second spring zone 37 increases greatly on account of the design. Consequently, further widenings of the carrier legs 12, 13 essentially act on the end section 42. This means that the spring characteristic of the spring part 3 also exhibits a second step in which the rigidity of the spring part 3 changes once more.

On account of the shaping of the carrier part 2, during bending of the carrier legs 12, 13 there are only relatively slight changes in the alignment of the transmitter unit 5 with respect to the receiver unit 6, so that a sufficient functional reliability can be ensured for the measurements that are to be carried out, for a very large opening width range of the carrier legs 12, 13.

By virtue of the clip-like configuration of the carrier part 2, the carrier legs 12, 13 come to bear flatly against an upper side and a lower side of the respective finger or toe opposite one another at their inner sides 18, 19. The side cheeks 20, 21 bring about centering of the finger or toe, as a result of which the sensor 1 has an increased lateral retention. Between the carrier legs 12, 13, the sensor 1 is open at the sides, as a result of which the build-up of sweat on the finger or toe is reduced. The shaping of the carrier part 2 is moreover selected such that the insertion depth for the finger or toe is limited. This is achieved in that the second carrier leg 13 forms an upward ramp 46 at its section adjoining the carrier base 14, on which ramp the tip of the finger or toe comes to bear when the optimal penetration depth is reached. In the preferred embodiment shown here, the carrier base 14 is configured in a U shape in longitudinal section, as shown in FIG. 2, as a result of which the carrier base 14 forms a hollow 47. In patients who have relatively long fingernails or toenails, this hollow 47 serves to accommodate the respective fingernail or toenail if the latter projects beyond the tip of the finger or toe. The measurement is therefore not impaired by relatively long fingernails or toenails.

Once the sensor 1 has been pushed onto the finger or toe of the patient, the sensor 1 is in principle sufficiently fixed on the finger or toe by the restoring force of the spring part 3, in order to be able to carry out the respective measurements in the correct manner. In order to avoid position changes of the sensor 1 relative to the finger or toe on account of voluntary or involuntary movements of the patient, additional fixing measures may be provided to secure the sensor 1 to the finger or toe. For example, for this purpose it is possible to use the fixing tape 48 shown in FIG. 1, which after the sensor 1 has been pushed on is wound around the finger or toe for example in the region of the end section 42 of the first spring leg 15 and thus surrounds the sensor 1. In a more comfortable solution, a fixing device may be provided on the carrier part 2, which fixing device makes it possible to better fix the sensor 1 on the finger or toe. By way of example, such a fixing device may be configured as a latching or clip closure which fixes the carrier legs 12, 13 relative to one another at the respective opening width. It is likewise possible to attach a Velcro closure to one of the carrier legs 12, 13, which Velcro closure is wound around the finger or toe after the sensor 1 has been pushed on.

By virtue of the simple design of the sensor 1 according to the invention, the latter may be configured for example as a disposable sensor. Suitable materials for the carrier part 2 are then relatively inexpensive polymers, such as crayton or TPE (santoprene). Materials that are suitable for the spring part are then comparatively inexpensive polymers, such as polystyrene, ABS or SAN. Inexpensive components can then be used for the optoelectronic elements, that is to say transmitter unit 5, receiver unit 6 and plug 9.

As an alternative, it is also possible to configure the sensor 1 according to the invention as a reusable multiway sensor. For the manufacture of the carrier part 2, higher-quality polymers such as silicone or polyurethane are then suitable. The spring part 3 may then likewise be manufactured from high-quality polymers, such as polyoxymethylene or polyamide. High-quality components which are suitable for multiple use are then used for the optoelectronic elements.

In summary, the present invention can be characterized in that the sensor 1 is composed of a relatively flexible carrier part 2, which is used to retain the transmitter unit 5 and the receiver unit 6, and of a relatively rigid spring part 3, which is arranged on the outside of the carrier part 2 and presses the latter against the finger or toe for measurement purposes. The U-shaped or C-shaped or clip-shaped configuration of the carrier part 2 and of the spring part 3 allows the sensor 1 to be used on fingers or toes of varying size, so that one and the same sensor 1 can always be used for different patient groups. As a result, the number of sensors manufactured may be increased and hence the price thereof will be reduced. The spring part 3 can be designed with a relatively low complexity such that the sensor 1 has a spring characteristic which always generates suitable application forces for fingers or toes of different size.

LIST OF REFERENCES 1 sensor
2 carrier part
3 spring part
4 signal transmission unit
5 transmitter unit
6 receiver unit
7 first cable
8 second cable
9 plug
10 collective cable
11 common cable
12 first carrier leg
13 second carrier leg
14 carrier base
15 first spring leg
16 second spring leg
17 spring base
18 inner side of 12
19 inner side of 13
20 side cheek of 12
21 side cheek of 13
22 central zone of 12
23 central zone of 13
24 groove
25 outer side of 12
26 outer side of 14
27 outer side of 13
28 first recess
29 second recess
30 cable channel
31 further cable channel
32 end section of 11
33 transmission opening in 28
34 receiving opening in 29
35 receiving contour of 2
36 first spring zone
37 second spring zone
38 region 39 support section
39a first support section
39b second support section
39c third support section
40 transition between 16 and 17
41 step
42 end section of 15
43 start section of 15
44 flattening
45 stop
46 ramp
47 hollow
48 fixing tape

The invention claimed is:

1. A medical sensor for measuring pulse blood tissue and/or skin parameters using electromagnetic waves for transmission, comprising:
a clip-like carrier part for pushing onto a patient's finger or toe from the front;
a first carrier leg that carries at least one transmitting element and bears with its inner side against the finger or toe during a measurement operation;
a second carrier leg that carries at least one receiving element and bears with its inner side against the finger or toe, opposite the first carrier leg, during the measurement operation;
a carrier base that connects the two carrier legs to one another in the region of a tip of the finger or toe;
a clip-like spring part having two spring legs and a spring base that connects the spring legs, wherein the spring part is arranged on the outside of the carrier part such that the first spring leg bears against an outer side of the first carrier leg and the second spring leg bears against an outer side of the second carrier leg;
wherein the carrier art is made of a more flexible material than the spring part;
wherein the spring legs prestress the carrier legs toward one another;
wherein the first spring leg has a start section that adjoins the spring base and an end section that is remote from the spring base; and
wherein the end section is more flexible than the start section.

2. A sensor as claimed in claim 1, wherein
the carrier part is made in one piece and/or
the spring part is made in one piece.

3. A sensor as claimed in claim 1, wherein
the spring part has at least one spring zone which connects together two support sections that adjoin it, and
the support sections are more rigid than the spring zone.

4. A sensor as claimed in claim 3, wherein the spring part has at least two spring zones with different spring elasticities.

5. A sensor as claimed in claim 4, wherein the support sections which adjoin the more flexible spring zone form a stop which restricts the bending deformation in this spring zone to a predefined extent during widening of the carrier legs.

6. A sensor as claimed in claim 3, wherein
a spring zone is made at a transition between the second spring leg and the spring base and/or
a spring zone is made approximately in the middle of the spring base.

7. A sensor as claimed in claim 3, wherein
the spring part has a first spring zone which is made at a transition between the second spring leg and the spring base,
the spring part has a second spring zone which is made approximately in the middle of the spring base, and
the second spring zone is more rigid than the first spring zone.

8. A sensor as claimed in claim 1, wherein
the carrier base is designed as a hollow configured to receive a fingernail or toenail during the measurement operation.

9. A sensor as claimed in claim 1, wherein
the inner sides of the carrier legs are curved in a concave manner transversely to a push-on direction, along which the sensor is pushed from an initial position onto a finger or toe,
on each carrier leg side cheeks project beyond a center zone, and
the spring part prestresses the carrier legs toward one another in such a way that the carrier legs bear against one another at their side cheeks prior to the sensor being pushed onto the finger or toe.

10. A sensor as claimed in claim 1, wherein on the outside of the carrier part there is a groove which extends from the outer side of the first carrier leg via an outer side of the carrier base to the outer side of the second carrier leg, in which the at least one transmitting element and the at least one receiving element are arranged and in which connection cables for the transmitting element and the receiving element are laid, and in which the spring part closes the groove from outside.

11. A sensor as claimed in claim 1, wherein the carrier part has a fixing device which allows fixing of the sensor on the finger or toe after the sensor has been pushed onto the finger or toe.

12. A sensor as claimed in claim 1, wherein the end section is more rigid than the second spring zone.

13. A sensor as claimed in claim 1, wherein the end section is connected to the start section in a region that is approximately central with respect to the second spring leg.

14. A medical sensor comprising:
a carrier part formed by two legs joined by a base and defining a region therein for placement of a patient part; and
a spring part formed by two legs joined by a base, wherein the spring part legs apply force to carrier part legs to secure the medical sensor on the patient part,
wherein the spring part further comprises at least two spring zones having different spring elasticities; and
wherein a first spring zone is formed by a material contraction to have a greater elasticity than a second spring zone.

15. The medical sensor of claim 14, wherein the first spring zone is made at a transition between one of the spring part legs and the spring part base and the second spring zone is made approximately in the middle of the spring part base.

16. The medical sensor of claim 15, wherein the first spring zone further comprises a stop beyond which the first spring zone cannot flex.

17. The medical sensor of claim 14, wherein the second spring zone is flattened to have a lesser elasticity than the first spring zone, and wherein the spring part flexes at the first spring zone until a spring stop is reached, thereafter the spring part flexes at the second spring zone.

18. A medical sensor comprising:
a carrier part defining a region therein for placement of a patient part; and a spring part that fits over the carrier part and applies force to secure the carrier part on the patient part;

wherein the spring part includes at least two spring zones having different spring elasticities and a spring stop, wherein the spring part flexes at a first spring zone until the spring stop is reached, thereafter the spring part flexes at a second spring zone.

19. The medical sensor of claim 18, wherein the first spring zone is made at a transition between a spring part leg and a spring part base and the second spring zone is made approximately in the middle of the spring part base.

20. The medical sensor of claim 18, wherein the carrier part further comprises two legs joined by a base, a transmitter located on a first of said legs, and a receiver located on a second of said legs.

* * * * *